United States Patent [19]

Delente

[11] 3,997,396
[45] Dec. 14, 1976

[54] METHOD FOR THE IN VITRO PROPAGATION AND MAINTENANCE OF CELLS

[75] Inventor: Jacques J. Delente, St. Louis, Mo.

[73] Assignee: Monsanto Company, St. Louis, Mo.

[22] Filed: July 2, 1973

[21] Appl. No.: 376,038

[52] U.S. Cl. .............................................. 195/1.8
[51] Int. Cl.$^2$ ........................................ C12K 9/00
[58] Field of Search ............................. 195/1.7, 1.8

[56] References Cited

UNITED STATES PATENTS

| | | | |
|---|---|---|---|
| 3,027,305 | 3/1962 | Freeman | 195/127 |
| 3,821,087 | 6/1974 | Knazek et al. | 195/127 |
| 3,873,423 | 3/1975 | Munder et al. | 195/1.8 |

OTHER PUBLICATIONS

Knazek et al.–*Science*–vol. 178, (Oct.–Dec. 1972), pp. 65 and 66.

Leighton–*J. of the U.S. National Cancer Inst.*, vol. 12, No. 3 (1951), p. 545.

*Primary Examiner*—Sam Rosen
*Attorney, Agent, or Firm*—Joseph D. Kennedy; Scott J. Meyer

[57] ABSTRACT

The propagation and/or maintenance of living cells in vitro is accomplished by attaching and growing cells on one side or surface of a hollow fiber membrane. The attached cells are propagated and/or maintained by passing oxygen through the membrane from the other side and into contact with the cells and simultaneously incubating the cells in a nutrient medium. This method is employed in tissue and cell culturing of altered and unaltered cells which attach to a surface for maintenance and growth.

12 Claims, No Drawings

METHOD FOR THE IN VITRO PROPAGATION AND MAINTENANCE OF CELLS

BACKGROUND OF THE INVENTION

1. Field of the Invention

This invention relates to a method for propagating and/or maintaining cells in vitro. More specifically this invention relates to a method for propagating cells on a surface of a hollow fiber membrane.

2. Description of the Prior Art

The cultivation of vertebrate animal cells in vitro i.e. apart from the host animal has long been known. It is generally considered that the first such cultivation was performed in the first decade of this century and involved the growth of infectious canine lymphosarcoma in blood.

In spite of long experience this art or science has come into prominence only in recent years. This prominence is mainly due to the demand for many types of vertebrate animal cells for use in medical and veterinary research and diagnosis, in culturing of infectious agents such as viruses, and in the production of hormones and other biological products. Presently this demand is especially high for mammalian cells, particularly normal mammalian cells which must be attached to a surface for growth, as opposed to growth in a suspension culture.

Numerous procedures have been developed for propagating and/or maintaining attached cells in vitro. Perhaps the most successful prior method involves attaching and growing cells on the interior surface of glass and plastic roller tubes and bottles. Another successful method is by attaching and growing cells on the flat side of appropriately shaped stationary bottles. Many types of cells have been grown by these and other prior art methods with such methods being most successful in growing abnormal or altered cells, that is, cells which possess an abnormal or different number of chromosomes from normal cells of the same type and which have the ability to regenerate an indefinite number of times. However these and other prior methods possess several serious drawbacks, especially in the economical production of large quantities of normal or unaltered mammalian cells. Normal cells in contrast to abnormal cells possess the normal number of chromosomes for the species and regenerate only a relatively predictable number of times before senescence or death.

The principal drawback of prior methods in the propagation of normal mammalian cells arises from the fact that with such methods it is difficult to provide aerobic conditions. Stated otherwise unless the oxygen supply is properly provided in adequate quantities to normal cells the cells will not maintain their normal, differentiated functional state. An additional drawback of prior methods in propagating attached cells, whether normal or abnormal, is the difficulty encountered in attaining tissue-like densities on the growing surface because of problems pertaining to nutrient diffusion within the tissues. Further, prior art methods are not readily adapted to large scale operations and thus are not economically suited for producing large quantities of cells.

OBJECTS

In view of the foregoing it is a primary object of the present invention to provide an improved method for propagating and/or maintaining normal mammalian cells in vitro under aerobic conditions.

Another object of the present invention is to provide an improved method of propagating cells in vitro in tissue-like densities.

A further object of the present invention is to provide an improved method for propagating cells in a manner by which such cells can be economically produced in large quantities.

A still further object of the present invention is to provide an improved method for supplying oxygen and nutrients to cells which are attached to a surface.

Other objects and advantages of the present invention will be apparent from the specification and appended claims.

SUMMARY OF THE INVENTION

It has been discovered in accordance with the present invention that cells are propagated by aseptically attaching cells to one wall of an oxygen permeable hollow fiber membrane and contacting the opposite wall of the hollow fiber membrane with an oxygen carrier thereby to cause oxygen to permeate through the membrane and to bring it into contact with the attached cells while simultaneously incubating the attached cells in a nutrient cell culture medium. By continuously passing oxygen through the membrane from the side opposite that on which cells are attached the method of the present invention permits a continuous and, if desired, uniform supply of oxygen to reach and nourish the cells thereby facilitating aerobic propagation of the cells in desired tissue densities.

DETAILED DESCRIPTION

In carrying out the method of the present invention the cells are aseptically attached to one wall or surface (exterior or interior) of the hollow fiber membrane by contacting cells suspended in a cell culture medium with the desired membrane wall. For the purpose of attachment the "cell culture medium" will typically be a nutrient medium for the cells, however a non-nutrient physiologically compatible medium such as physiological saline can also be employed if desired. Upon attachment (and during attachment if desired) oxygen is supplied to the cells by contacting the opposite side of the membrane with an oxygen carrier. Simultaneously the cells are incubated in a nutrient cell culture medium.

In a preferred embodiment the cells are attached to and grown on the exterior wall of a hollow fiber which is preferably open at both ends. By this procedure it is possible to continuously pass a stream of an oxygen carrier through the hollow core of the fiber. The continuous passage of oxygen carrier through the core of a continuously hollow fiber may be accomplished by passing the oxygen carrier through the fiber in uniform amounts or by pulsating the oxygen carrier through the fiber. Pulsation is peferred in order to obtain optimum distribution of oxygen to all cells and to minimize channeling of oxygen.

In an alternate procedure the continuously hollow fiber may be closed at one end. In this procedure the oxygen carrier is passed into the core of the fiber and oxygen is diffused through the wall and thus brought into contact with the cells.

In the method of the present invention any suitable oxygen carrier may be employed. Generally air is the preferred oxygen carrier however carriers containing dissolved oxygen such as silicone polymers, hemoglobin, fluorocarbons, and oxygenated nutrient medium may also be used with desired results. When air or other suitable gaseous mixtures of nitrogen and oxygen are employed it is also preferred that the gas contain small amounts of carbon dioxide e.g. on the order of 2-5%. The carbon dioxide serves to provide carbonate buffering and thereby assists in maintaining the pH of the medium on the other side of the membrane within the desired range.

The cells are incubated in a nutrient cell culture medium under cell growth maintenance conditions of pH and temperature. Suitable nutrient cell culture media are known to the art and such may be used in the method of the present invention. Typically such nutrient culture media contain the known essential amino acids, vitamins, carbohydrates, mineral salts and, preferably, blood serum. Fungicides and bacteriacides may also be included in such media in desired amounts to prevent the growth of undesired microorganisms. As indicated above the pH of the nutrient medium is advantageously controlled within the desired range (typically in the range of 6.8-8.2) by including small amounts of carbon dioxide in the oxygen carrier. However if desired the pH can be controlled by including a suitable buffer such as HEPES buffer (a mixture of N-2-hydroxyethyl piperazine and N'-2-ethane sulfonic acid) in the nutrient cell culture medium itself. Other suitable methods for controlling pH such as passing the medium over ionic exchange resins may also be employed.

The choice of temperature for incubation of cells is within the skill of the worker in the field of cell and tissue culturing and will depend principally upon the physiological temperature for the particular cells to be propagated, that is the optimum temperature at which growth or maintenance of the cells occurs. For example when normal mammalian cells are propagated a narrow temperature range of from about 35°–40° C is typically employed whereas, for example, if the cells are reptilian in origin lower or higher temperatures may be employed.

The method of the present invention utilizes hollow fiber membranes. The hollow fiber membranes may be employed in any suitable fashion such as for example in bundles, in single strands or in mesh relationship. The hollow fiber is, of course, designed to be permeable to gas, but impermeable to the cells. The membrane can be of a dense or of a "Loeb" structure. The hollow fiber may be produced from any suitable material which is non-toxic to the cells which can be appropriately spun into fibers and which permits cell attachment thereto. Examples of such materials include polyolefins such as polyacrylonitrile and polystyrene, polyionic polymers, polycarbohydrates such as cellulose, and cellulose derivatives, for example, cellulose esters, polypeptides such as collagen, silicone rubber polymers, fluorocarbon polymers etc. and the like. It has been found that cell attachment to the surface of the membrane is promoted when the membrane possesses increased surface energy as is evidenced by the presence of positive or negative charges. Attachment of cells to an otherwise suitable membrane may be promoted by coating the surface to which the cells are to be attached with collagen.

The optimum dimensions for the hollow fibers may vary depending among other things on the apparatus and the oxygen carrier employed. Generally the inside diameter of the hollow fiber is in the range of from about 10 to about 300 microns with an inside diameter of 50–100 microns being preferred. The membrane wall must of course be sufficiently thin to permit permeation as desired and sufficiently thick so as to not rupture under the conditions employed. Typically suitable membranes have an effective wall thickness of from about 10 to about 100 microns.

Suitable cells for propagation in accordance with the method of the present invention include tissue cells from vertebrate animals which are capable of attachment and growth or maintenance on a surface. Of course cells which are inherently incapable of proliferation such as erythrocytes cannot be employed in the method of this invention. Examples of such suitable cells include diploid cell lines such as W1-38 human lung fibroblasts, MRC-5 male human fetal lung fibroblasts and DBS-FRh L-2 rhesus monkey fetal lung fibroblasts; primary cells such as bovine and human anterior pituitary cells, chicken embryo, frog epithelium and rat liver; and established cell lines such as Hela human cervix (carcinoma) cells, rhesus monkey kidney cells (LLC-$MK_2$) Syrian baby hampster kidney cells(BHK-21) etc. and the like.

It will be appreciated that the above list of cells is given for illustrative purposes and that other cells from other sources including avian, mammalian, reptilian and amphibian sources including normal and abnormal cells can be propagated and maintained in accordance with the method of the present invention.

The following examples illustrate specific embodiments of the invention. In the examples the preparation of the cells, the preparation of the innoculum, and the cell culturing experiments were carried out under sterile conditions.

EXAMPLE 1

Preparation of Cells

One calf pituitary obtained by dissection from a freshly slaughtered animal was stored approximately four hours in phosphate buffered salts (PBS) medium of the following composition:

| | | |
|---|---|---|
| NACl | grams | 8.0 |
| KCl | '' | 0.2 |
| $Na_2HPO_4$ | '' | 1.15 |
| $CaCl_2$ | '' | 0.1 |
| $KH_2PO_4$ | '' | 0.2 |
| $MgCl_2 . 6H_2O$ | '' | 0.1 |
| Penicillin | * | 100,000 |
| Streptomycin | grams | 0.1 |
| Distilled Water | mls. | 900 |

*I.U.

The temperature of the medium during storage was about 25° C. The anterior portion was dissected from the gland, cleaned to remove connective tissue and minced. The minced anterior gland was gently mixed with an aqueous solution of trypsin in a Petri dish and the resulting mixture was allowed to stand under sterile conditions for 18 hours at room temperature to obtain release of individual cells into the fluid. The aqueous trypsin solution was prepared by mixing 10 millileters of PBS with 250,000 units of dry powdered trypsin enzyme sold under the name TRYPTAR by Armour and Co., Chicago, Ill. and 0.75 ml. of 0.5 normal sodium hydroxide. The released pituitary cells (epithelia) were separated from remaining connective tissue by repeated centrifugation, filtration and washing. It was determined from a cell count (with a hemocytometer) that the resulting washed cell suspension contained $1.37 \times 10^6$ cells per ml.

Preparation of Innoculum

To prepare the innoculum 30 mls. of the washed cell suspension were diluted to 150 mls. with Basal Medium Eagle's (BME) containing 10% fetal calf serum. The composition of the Basal Medium Eagle's (BME) constituting 90% of the $BME_{90}$ fetal $calf_{10}$ was as follows:

|  | Mg/l. |
| --- | --- |
| l-arginine chlorhydrate | 105 |
| l-cystine | 24 |
| l-histidine monohydrochlorhydrate | 31 |
| l-isoleucine | 52 |
| l-lysine chlorhydrate | 58 |
| l-leucine | 52 |
| l-methiomine | 15 |
| l-phenylalanine | 32 |
| l-threonine | 48 |
| l-tryptophan | 10 |
| l-tyrosine | 36 |
| l-valine | 46 |
| choline chloride | 1.00 |
| Folic acid | 1.00 |
| Isoinositol | 1.00 |
| Nicotinamide | 1.00 |
| Pantothenic acid | 1.00 |
| Pyridoxal | 1.00 |
| Thiamine | 1.00 |
| Riboflavin | 0.10 |
| NaCl | 6800 |
| KCl | 400 |
| $NaH_2PO_4 \cdot 2H_2O$ | 150 |
| $NaHCO_3$ | 2000 |
| $CaCl_2$ | 200 |
| $MgCl_2$ | 200 |
| Glucose | 1000 |
| l-glutamine | 212 |
| Phenol ured | 20 |
| Penicillin | (1) |
| Streptomycin | 50 |

(1)50,000 I.U.

Reactor

The culturing of cells was carried out using a cell culture reactor consisting of a bundle of 100 open ended continuously hollow polymeric fibers, in a U position in a 10 ml. glass flask. The two ends of the fiber bundles are fitted in separate holes of a three-holed rubber stopper with the stopper being positioned in the neck of the flask. The third hole of the stopper is available for introduction and extraction of medium. The hollow fiber material is a commercial polyiomic polymer material sold under the name Amicon X M-50 by Amicon Corp., Lexington, Mass. Each fiber is 10 cms. in length and has approximately ½ sq. cm. of cell growing surface. Each fiber has an internal diameter of 360 microns and a wall thickness of 80 microns with the wall having a "Loeb" configuration.

Cell Culturing

The reactor was sterilized using Beta-propiolactone vapors and then rinsed with phosphate buffer. Innoculum (8 millileters) prepared above was introduced into the reactor to attach cells to the outer walls of the fibers. The reactor was placed in a jacketed carbon dioxide incubator and the contents were incubated for 49 days at 37° C. Throughout the 49 day incubation period a filtered mixture of air with 3% carbon dioxide was pumped (with an air pump) through the interior of the hollow fibers. During incubation the medium was changed at 2 day intervals. The withdrawn medium was collected and retained for analysis. On completion of the incubation period the medium was withdrawn from the reactor and a heavy confluent growth of cells on the hollow fibers was observed. The cells were then prepared for microscopic examination by formaldehyde fixation and staining on the fibers. It was observed by microscopic examination that the cells were normal. The retained media was analyzed for lactic acid and growth hormone. The analysis showed that the total retained media contained 700 nanograms of growth hormone and that the media were substantially free of lactic acid. The substantial absence of lactic acid indicates that the cell growth was achieved under aerobic conditions.

As a control 10 mls. of the above-prepared cell innoculum medium was placed in each of two T-flasks and the medium was incubated in the jacketed carbon dioxide reactor at 37° C for 49 days (simultaneously with the cell culture reactor). Medium was changed at two day intervals and the withdrawn medium was collected and retained. The area of growth for each T-flask was 50 sq. cms. The retained media was analyzed for growth hormone and lactic acid. The analysis showed that the combined media from both flasks contained 800 nanograms of growth hormone, (an average of 400 nanograms per flask) and that the production of lactic acid (based on glucose) was quantitative. The quantitative production of lactic acid indicates anaerobic cell growth condition.

EXAMPLE 2

In this example the cell culture reactor employed is of the type described in the U.S. Pat. No. 3,228,877 issued Jan. 11, 1966 to H. I. Mahon. The reactor consists of a bundle of 1000 continuously hollow fibers (Amicon XM-50) having a total external surface area of about 900 sq. cms. contained in a tubular casing. The hollow fibers are open at each end to permit continuous flow of the oxygen carrier. A cell innoculum medium of porcine pituitary cells ($7.6 \times 10^5$ cells per ml) was prepared following the procedure of Example 1. The cell culture reactor was innoculated with 33 mls. of innoculum medium to attach cells to the outer surface of the fibers. Incubation at 37°C was conducted for six days to produce a confluent growth of cells under aerobic conditions on the fibers. During the 6 day period air with 3% carbon dioxide was passed through the fibers in a pulsating manner (1 pulse every 10 seconds) at a rate of 5 cc. per minute. Throughout the 6 day period the cell culture medium was continuously charged. After initial introduction of the innoculum the medium change was accomplished by continuously pumping medium ($BME_{99}$Fetal $Calf_1$) into the reactor in contact with the exterior walls of the fibers at the rate of 4 mls. per minute and out of the reactor (excluding medium discharged through the fibers) at the rate of 1 ml. per minute. By this procedure medium flows radially through the cell layers, through the walls of the fibers and into the hollow cores of the fibers. Discharged medium was analyzed and found to contain growth hormone.

Radial flow of medium as in the procedure of this Example provides for the optimum distribution of nutrients to the cells thus aiding in the formation of dense cell layers. Since with radial flow the smaller molecules more readily permeate the hollow fiber membrane than do the larger molecules, the procedure further serves to concentrate large molecules (fetal calf serum, hormones and other metabolites) on the other side of the membrane.

EXAMPLE 3

The general procedure of Example 2 was repeated with the exception that the oxygen carrier was oxygenated Basal Medium Eagle's without serum which was pumped through the interior of the hollow fibers at the rate of 12 mls. per minute. The incubation was carried out for 12 days. Heavy confluent cell growth was observed on the fibers. Cell growth was aerobic during the first four days and anaerobic thereafter.

EXAMPLE 4

Human embryonic lung fibroblasts (WI-38 cells at 26th generation isolated by L. Hayflick) were incubated following the general procedure of Examples 2 and 3 for 24 days at 37° C in a cell culture reactor consisting of a bundle of polymeric hollow fibers (Amicon XM-50 polymer) in a rectangular casing. The fibers are open at each end to permit continuous flow of oxygen carrier. The pH of the cell culture medium throughout the 24 day incubation period fluctuated in the range of from about 7.2 to about 7.9. The hollow fiber bundle had a total external surface area of about 85 cm$^2$ of which about 65 cm$^2$ of the surface area was continuously immersed in medium throughout the 24 day incubation period. The cells were attached to the external walls of the fibers as in Example 2 with approximately 58% of the cells being attached to the external walls of the fibers after 18 hours. The cell density on the fibers after the 18 hour period was 1.56 × 10$^4$/cm$^2$ of surface. On completion of the 18 hour attachment period medium was pumped into and through the reactor in contact with the exterior walls of the fibers at the rate of 4 mls/hour and oxygen carrier (air + 3% CO$_2$) was passed through the fibers at the rate of 40 mls/hour. To obtain optimum contact of medium with the cells the fibers in the bundle were maintained in a spread position and the medium was pumped into the reactor perpendicular to the fibers. Confluent growth of cells on the fibers was obtained after 10 days of incubation with a cell density of 1 – 1.5 × 10$^5$ being observed. After the 14th day of incubation the cell density was 7.5 × 10$^5$ cells/cm$^2$. The cells were maintained for an additional 10 days with no increase in cell density being observed after the 14th day of incubation. After the 24 day incubation period the cells were removed from the fibers by trypsinization. The cells gave a normal appearance upon microscopic examination.

While the invention has been described with reference to particular embodiments thereof it will be appreciated that modifications and variations are possible without departing from the invention.

What is claimed is:

1. A method for propagating or maintaining cells in vitro which comprises (a) contacting a suspension of cells in a cell culture medium with the exterior wall of a non-toxic, oxygen permeable, hollow, fiber membrane thereby to attach cells to said wall of said hollow fiber membrane and (b) contacting the opposite wall of said membrane with an oxygen carrier thereby to cause passage of oxygen through the said membrane and bring said oxygen into contact with the attached cells on the other side of the membrane and simultaneously incubating the cells in a nutrient cell culture medium under cell growth or maintenance conditions of pH and temperature, with oxygen being supplied in adequate quantities to provide aerobic conditions continuously to maintain cells in their normal, differentiated functional state.

2. A method for propagating or maintaining cells in vitro which comprises (a) providing a suspension of cells in a cell culture medium (b) contacting said suspension with the exterior wall of a non-toxic, oxygen permeable, continuously hollow, fiber membrane said hollow fiber membrane having open ends, said open ends being inaccessible to said suspension, thereby to attach cells to said exterior wall of said fiber membrane and (c) passing an oxygen carrier through the interior of said hollow fiber thereby to cause permeation of oxygen through the said fiber membrane and bring said oxygen into contact with the attached cells and simultaneously incubating the cells in a nutrient cell culture medium under cell growth or maintenance conditions of pH and temperature, with oxygen being supplied in adequate quantities to provide aerobic conditions continuously to maintain cells in their normal, differentiated functional state.

3. The method of claim 2 wherein the cells are normal mammalian cells.

4. The method of claim 3 wherein the normal mammalian cells are human cells.

5. The method of claim 3 wherein the normal mammalian cells are pituitary cells.

6. The method of claim 2 wherein the oxygen carrier comprises air.

7. The method of claim 2 in which the nutrient medium is introduced externally of the fibers.

8. The method of claim 7 in which medium is provided in a manner so that medium flows through the walls of the fibers and into the hollow cores.

9. The process of claim 2 in which the oxygen carrier is pulsated through the fiber.

10. A method for propagating or maintaining cells in vitro which comprises (a) contacting a suspension of cells in a cell culture medium with the exterior wall of a non-toxic, oxygen permeable, hollow, fiber membrane thereby to attach cells to said wall of said hollow fiber membrane and (b) contacting the opposite wall of said membrane with a gaseous oxygen carrier thereby to cause passage of oxygen through the said membrane and bring said oxygen into contact with the attached cells on the other side of the membrane and simultaneously incubating the cells in a nutrient cell culture medium under cell growth or maintenance conditions of pH and temperature, with oxygen being supplied in adequate quantities to provide aerobic conditions continuously to maintain cells in their normal, differentiated functional state.

11. A method for propagating or maintaining cells in vitro which comprises (a) providing a suspension of cells in a cell culture medium (b) contacting said suspension with the exterior wall of a non-toxic, oxygen permeable, continuously hollow, fiber membrane said hollow fiber membrane having open ends, said open ends being inaccessible to said suspension, thereby to attach cells to said exterior wall of said fiber membrane and (c) passing a gaseous oxygen carrier through the interior of said hollow fiber thereby to cause permeation of oxygen through the said fiber membrane and bring said oxygen into contact with the attached cells and simultaneously incubating the cells in a nutrient cell culture medium under cell growth or maintenance conditions of pH and temperature, with oxygen being supplied in adequate quantities to provide aerobic conditions continuously to maintain cells in their normal, differentiated functional state.

12. The method of claim 11 in which the carrier is air.

* * * * *